United States Patent [19]

Rosen et al.

[11] Patent Number: 4,559,823
[45] Date of Patent: * Dec. 24, 1985

[54] DEVICE AND METHOD FOR MEASURING THE ENERGY CONTENT OF HOT AND HUMID AIR STREAMS

[75] Inventors: Howard N. Rosen; Albert C. Kent; George F. Girod, all of Carbondale, Ill.

[73] Assignee: The United States of America as represented by the Secretary of Agriculture, Washington, D.C.

[*] Notice: The portion of the term of this patent subsequent to Jul. 24, 2001 has been disclaimed.

[21] Appl. No.: 662,378

[22] Filed: May 30, 1984

[51] Int. Cl.$^4$ .......................................... G01N 25/62
[52] U.S. Cl. ..................................... 73/338; 73/338.3
[58] Field of Search ......................... 73/338, 338.3, 29

[56] References Cited

U.S. PATENT DOCUMENTS

| | | |
|---|---|---|
| 1,601,243 | 9/1926 | Irwin . |
| 2,107,077 | 2/1938 | Magner . |
| 2,623,391 | 12/1952 | Malecki . |
| 3,196,683 | 7/1965 | Gross . |
| 3,459,034 | 8/1969 | Kawaguchi . |
| 3,515,001 | 6/1970 | Greenspan et al. . |
| 3,603,135 | 9/1971 | Kawaguchi . |
| 3,886,797 | 6/1975 | Bauer . |
| 4,129,250 | 12/1978 | Chaikin et al. . |
| 4,222,261 | 9/1980 | Leblanc et al. . |
| 4,461,167 | 7/1984 | Kent et al. .................... 73/338 X |

OTHER PUBLICATIONS

Nantou et al., *Multichannel Digital Ventilated Psychrometer Using Eight–Bit Microcomputer*, In IEEE Trans. on Instr. and Meas., vol. IM-30, No. 2, pp. 98–102, Jun. 1981.

Zagorzycki, "Automatic Control of Conveyor Driers", Chemical Engineering Practice 75(4), 50 (1979).

*Primary Examiner*—Stewart J. Levy
*Assistant Examiner*—Joseph W. Roskos
*Attorney, Agent, or Firm*—M. Howard Silverstein; David G. McConnell

[57] ABSTRACT

A portable device and method for measuring enthalpy and humidity of humid air from a space or flow channel at temperatures from 80° to 400° F. is described. The device consists of a psychrometer for measuring wet-bulb temperature, a vacuum pump for inducing sample air flow through the unit, a water-heating system for accurate psychrometer readings, an electronic computer system for evaluation of enthalpy and humidity from corrected and averaged values of wet- and dry-bulb temperatures, and a monitor for displaying the values. The device is programmable by the user to modify evaluation methods as necessary.

5 Claims, 5 Drawing Figures

DEVICE AND METHOD FOR MEASURING THE ENERGY CONTENT OF HOT AND HUMID AIR STREAMS

BACKGROUND OF THE INVENTION

This invention relates to a portable device and method of measuring enthalpy or heat content of humid air streams.

Many industrial processes involve the flow of humid air to or from the pieces of equipment. Generally, such processes are involved in removal of water from a product (drying) or the re-entry of water to improve the physical properties of the product (conditioning). Considerable energy is transferred in the humid air streams of these processes.

When designing or modifying existing equipment, a knowledge of the heat entering the leaving the equipment is essential for efficient operation. The need for such information is more critical in processes where stream temperatures go above 200° F. because of the potential for energy recovery from these streams for further use in a processing plant.

We know of no device which measures the energy content of humid air streams. Energy content of air streams are usually evaluated indirectly by heat and mass balances on a process from measurements of temperatures, input energy, and humidities.

In humid air streams above 200° F., the amount of water vapor in the air can contribute significantly to the total heat content of the stream. Therefore, it is essential that humidity content be accurately measured. We previously developed a psychrometer for measuring the humidity of a gas flow up to 500° F. dry-bulb and 210° F. wet-bulb temperature. This device has a double-wick wet-bulb sensor, which enables accurate and rapid determination of humidity at temperatures above 200° F. The double-wick concept for measuring wet-bulb temperatures was used in modified form to develop the instant energy measuring device.

Numerous forms of psychrometer are known in the prior art. The most relevant prior art of which the applicants are aware may be summarized as follows.

U.S. Pat. No. 1,601,243 to Irwin describes an early form of psychrometer in which the incoming air is heated by means of an electric heater. The psychrometer is intended for use at substantially ambient temperatures, the purpose of the heating being to prevent the formation of ice around the wet bulb.

U.S. Pat. No. 2,107,077 to Magner describes a psychrometer in which the wet bulb has a wick surrounded by a sock so that the gas the humidity of which is being measured passes over the sock and keeps the water supplied to the wet bulb at substantially the same temperature as the gas stream. This form of psychrometer is, however, capable of operating only at relatively low temperatures.

U.S. Pat. No. 2,623,391 to Malecki describes a psychrometer in which the wet bulb is surrounded by a mass of porous material to improve thermal conductivity to the wet bulb and thus to secure better sensitivity and quicker response to vapor concentration changes.

U.S. Pat. No. 3,196,683 to Gross describes a psychrometer in which, to prevent excessive evaporation of water from the wick and consequent fouling thereof at the point where the wick is exposed to the air flow, the wick is enclosed within a tube which is split so as to allow only an extremely small area of contact between the wick and the air flow.

U.S. Pat. No. 3,459,034 to Kawaguchi describes a psychrometer for measuring the moisture content of a gas at high temperatures in which a sample of gas is admitted to a measuring chamber and a wet bulb within the chamber is supplied with water from a reservoir which is kept cooled below the boiling point of water.

U.S. Pat. No. 3,515,001 to Greenspan, et al. describes a psychrometer for measuring the humidity of a stream of gas containing vapor of a condensible liquid in which a sample stream of the vapor/gas mixture is flowed over the wick and a heat exchanger, while a stream of liquid corresponding to the condensed vapor of the vapor/gas mixture is counterflowed through the heat exchanger to the wick.

U.S. Pat. No. 3,603,135 to Kawaguchi describes a high-temperature psychrometer in which the wet bulb is detachably inserted into a sleeve made of a temperature-resistant capillary material, the base portion of this sleeve being exposed to the passage of water in a predetermined amount and at a predetermined pressure so that the sleeve is maintained in a reproducibly wet condition.

U.S. Pat. No. 3,886,797 to Bauer describes an electrical-resistance psychrometer provided with means for uniform supply of an evaporating liquid from a supply tank to an evaporator body made of a porous material which surrounds the "wet" resistor, this wet resistor having an appreciable electric current passed therethrough so as to increase its temperature.

U.S. Pat. No. 4,129,250 to Chaikin, et al. describes a psychrometer intended for measuring the humidity of exhaust air from industrial driers (and thus capable of operating at moderately high temperatures) in which a wet bulb thermocouple is physically dipped into a bowl of water under the cotrol of a timer system to control the amount of exhause air discarhed until the wet bulb thermocouple is equilibrated with the exhause air sampled after dipping.

U.S. Pat. No. 4,222,261 issued Sept. 16, 1980 to Leblanc, et al. describes a high-temperature psychrometer in which the wet bulb is surrounded by a sheath of porous material, which is in turn surrounded by a screen to prevent thermal radiation evaporating too much liquid from the sheath. A dosing pump is provided for injecting predetermined amounts of volatile liquid at regular intervals into the interior of the sheath and onto the screens to ensure sufficient moistening of the sheath and the screens.

Zagorzycki, "Automatic Control of Conveyor Driers", Chemical Engineering Practice 75(4), 50 (1979) discusses the drying of food products and the limitations of prior art psychrometers.

SUMMARY OF THE INVENTION

The invention provides a portable device which directly measures dry-bulb and wet-bulb temperatures to evaluate the heat content and humidity ratio of humid air streams. Each of these values is displayed on a monitor screen. This device is portable and can handle humid air streams from 80° to 400° F. dry-bulb temperature and 40° to 210° F. wet-bulb temperature. All components are easily accessible for cleaning and the cloth wicks of the psychrometer section are easily replaceable.

The benefits and advantages of the present invention are achieved by an apparatus and method in which humid air is drawn into the psychrometer of the unit by negative pressure. The psychrometer has a sensing device which accurately masures dry- and wet-bulb temperatures. The humid air is drawn out of the psychrometer to preheat the water supply to the psychrometer to within 5° F. of the wet-bulb temperature. Electric analog signals from the psychrometer dry- and wet-bulb temperatures are converted to digital signals for evaluation of enthalpy and humidity ratio by a microprocessor. Several values are read and averaged to reduce random sampling error. Values are displayed on a monitor screen. The unit is also programmable so that the user can change the relationships for evaluation and averaging in the determination of enthalpy, humidity ratio, and temperatures.

Additional features and advantages of the invention will become apparent from the following description, which is not presented by way of limitation.

DETAILED DESCRIPTION

Figure 1:
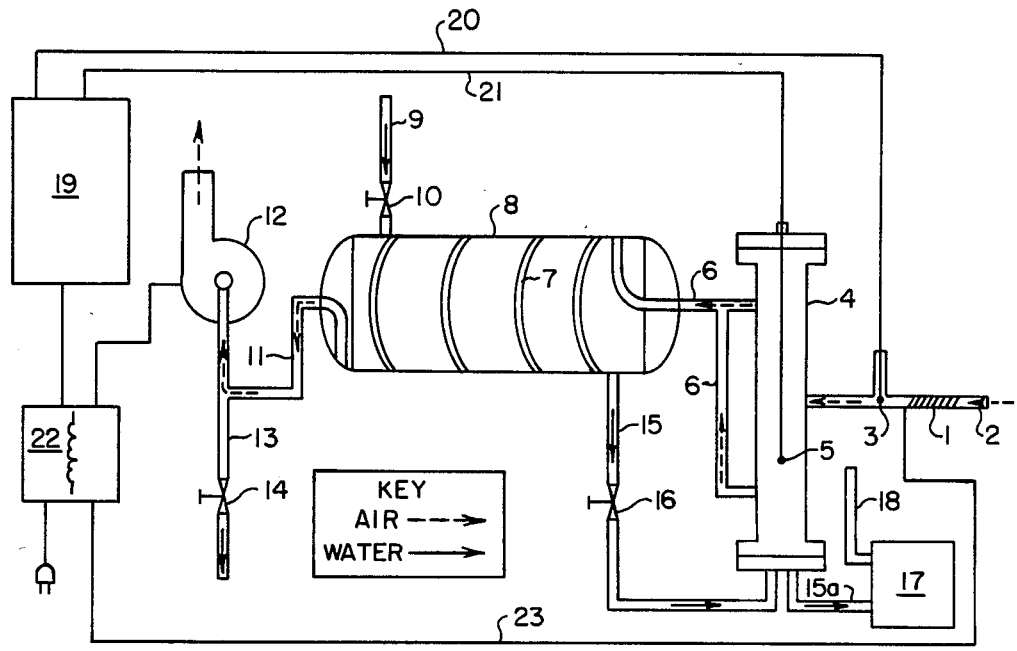
FIG. 1 is a diagramatic sketch of the sampling and computer system for the energy-measuring device.

Referring to FIG. 1, a temperature-controlled electric resistance heater 1 is wrapped around sample inlet air line 2 to keep the sample air above the dew point temperature. A resistance thermometer-RTD-3 is placed in the sample inlet air line 2 to measure inlet dry-bulb temperature. The inlet line connects to a psychrometer 4 which contains a wet-bulb sensing device 5. A dual sample exit air line 6 connects to a heating coil 7 which surrounds the water preheater tank 8. Sample air leaves the heating coil 7 through line 11 to a vacuum pump 12 which draws sample air through the unit with negative pressure. Condensate formed in the system leaves through the condensate drain line 13 and is controlled by the condensate drain valve 14.

A water fill line 9 leading to tank 8 is regulated by a water fill valve 10 and is used to replace water as it is slowly consumed by the psychrometer 4. Preheated water flows from the water preheater tank through water line 15 controlled by water line valve 16 through to the psychrometer 4. Excess water is psychrometer 4 is removed through drain line 15a to the water overflow tank 17, which has an air vent 18 to prevent back pressure buildup.

An electronic display computer 19 receives electric signals via dry-bulb temperature RTD line 20 and wet-bulb temperature RTD line 21. A conventional power supply 22 drives the electronic display computer 19, the vacuum pump 12, and the inlet air heater 1 via heater line 23.

Figure 2:
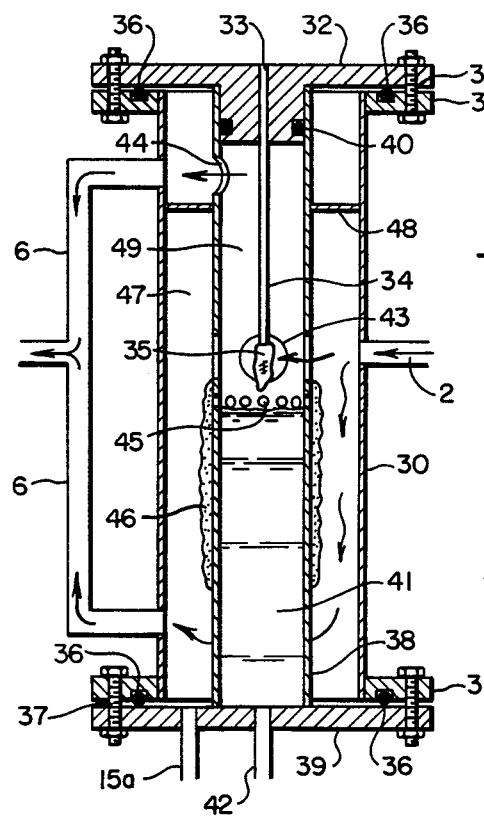
FIG. 2 is a diagramatic sketch of the psychrometer.

As seen in FIG. 2, the psychrometer 4 consists of a hollow outer cylinder or housing 30 with flanges 31 at the top and bottom. The wet-bulb sensor 5 extends through a sensor support tube 34 mounted in a hole 33 in top flange 32 which is secured to flange 31 by a plurality of bolts 37. Covering the wet-bulb sensor is a wet-bulb wick 35.

An outer O-ring 36 forms the seal between the top outer flange 32 an the innter flange 31.

An inner water supply tube 38 is connected to the psychrometer 4 by a bottom outer flange 39 secured in place by additional bolts 37. The top and bottom of flanges 32 and 39 are each sealed against the top and bottom flanges 31 of the cylinder 30 with an O-ring 36 and 40, respectively.

Water 41 is supplied through water inlet line 42 which is connected to water line 15. The inlet water supply tube 38 contains an inner air flow channel entrance port 43 where sample air is provided to the wet-bulb sensor 5, an inner air flow channel exit port 44, where airs leaves the wet-bulb sensor area, and water supply overflow ports 45, where water is supplied to an outer wet-bulb water supply wick 46. This outer wick 46 brings the supply water temperature to within 5° F. of the wet-bulb temperature. An outer annular flow channel 47 is formed by the bottom outer flange 39, the outer cylinder 30, the inner water supply tube 38, and an annulus seal 48. Air flow baetween the outer flow channel 47 and the inner flow channel 49, formed by the water 41, the wet-bulb sensor mounting 32, and the inner water supply tube 38, is through entrance port 43. A drain line 15a is provided to remove excess overflow water.

Figure 3:
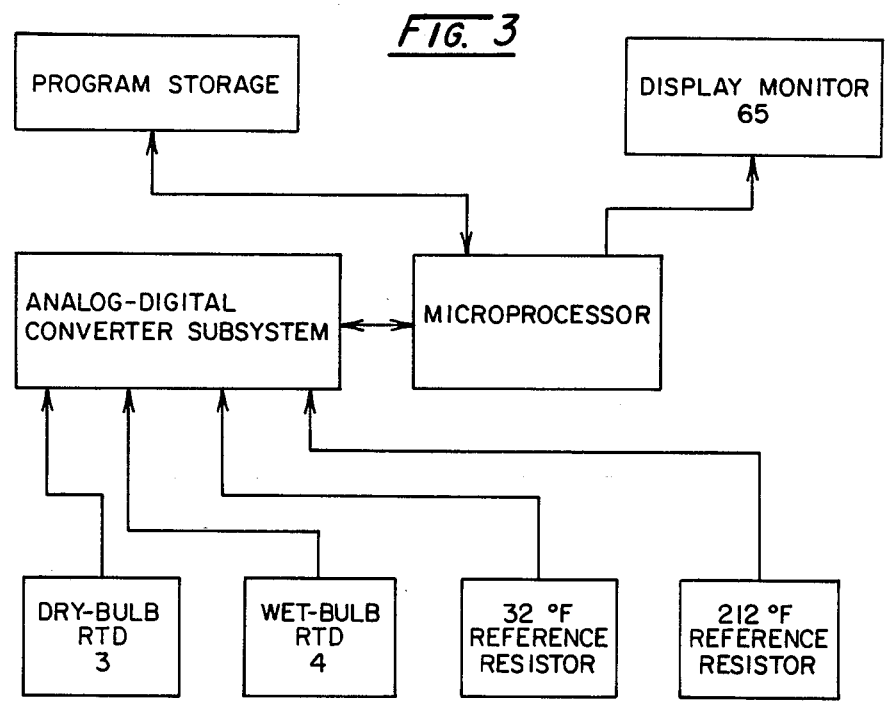
FIG. 3 is an electronic schematic diagram for evaluating and displaying energy content and humidity ratio from wet- and dry-bulb temperatures.

FIG. 3 shows the path of electrical signals from the dry-bulb 3 and wet-bulb 4 RTD's and also from two reference resistors to approximate the temperature at 32° F. and 212° F. and thus provide measurement error correction. These signals are converted from analog to digital form before being fed into a microprocessor with at least 8K memory. The microprocessor calculates humidity ratio and enthalpy from the following equations based on those found from *ASHRAE Handbook, 1981 Fundamentals;*

$$Y = \frac{(1093 - 0.556 T_{wb}) Y_s - 0.240 (T_{db} - T_{wb})}{1093 + 0.444 T_{db} - T_{wb}}$$

$$H = 0.240(1 + 8.33 \times 10^{-6} T_{db}) T_{db} +$$

$$Y[1061 + 0.444(1 + 4.464 \times 10^{-6} T_{db}) T_{db}]$$

where:

$Y_s = 0.622 P_s / (14.7 - P_s)$ is the saturation humidity in lb water/lb dry air.

$P_s = 0.000145$ $exp[-5800/T + 1.391 - 0.04864T + 0.4176 \times 10^{-4} T^2 - 0.1445 \times 10^{-7} T^3 + 6.546 \ ln(T)]$ is the saturation pressure of water at $T_{wb}$ in psi.

$T = (T_{wb} + 459.6)/1.8$ is a conversion factor.

Y is the humidity ratio in lb/water/lb dry air.

H is the enthalpy based on 0° F. in Btu/lb dry air.

$T_{db}$ is the dry-bulb temperature in °F.

$T_{wb}$ is the wet-bulb temperature in °F.

The microprocessor drives the program storage (cassette recorder, for example) and a display monitor (small television, for example).

Figure 4A:
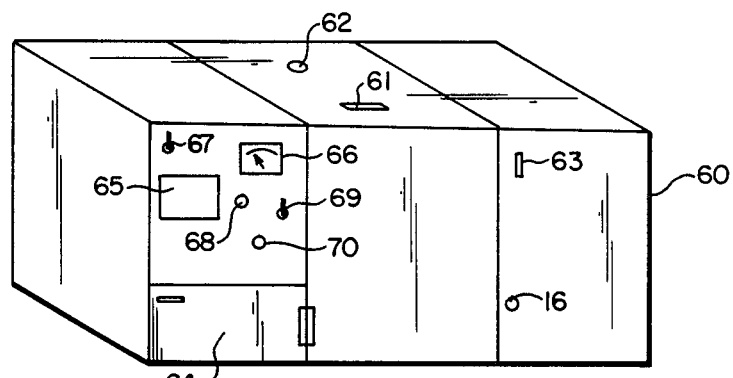
FIG. 4a is an orthogonal front view of the exterior of the energy-measuring device.
Figure 4B:
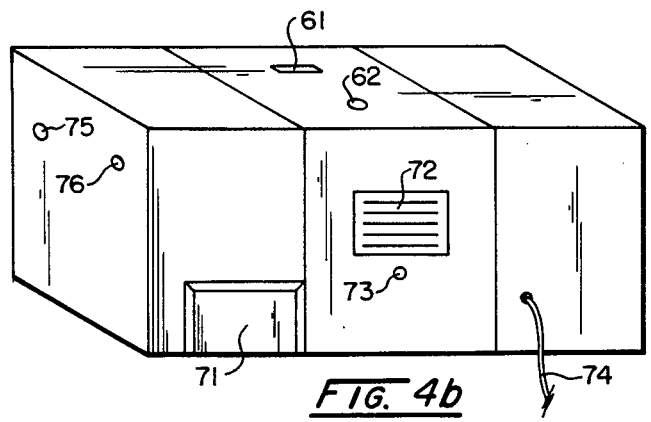
FIG. 4b is an orthogonal rear view of the exterior of the energy-measuring device.

Details of the exterior of the energy-measuring device are described in FIGS. 4a and 4b. Thin metal sheets 60 with insulated backing enclose the device. The wet-bulb water feed input port 61 and vacuum pump motor intake 62 for cooling air are on top of the housing. A level indicator 63 for the water preheater tank 8 and the handle of the water line valve 16 protrude through a front panel. A compartment for housing the computer 64 is located in the lower front of the device above which is the electrical control panel; comprised of a display monitor 65, a temperature gauge for the inlet sample air line 66, a vacuum pump switch 67, a monitor adjustment knob 68, and an inlet sample line temperature control on-off switch 69 and temperature controller 70. The reverse side of the device contains a compartment 71 for the feed water overflow tank 17, a grill 72 covering the exhaust port for vacuum pump cooling air and sample air, the outlet port 73 for the condensate drain line 13, and an electrical power line 74. On the side of the device is the sample line input port 75 and a control plug 76 for the temperature-controlled resistance heater 1.

During operation of the energy-measuring device, air is drawn from a flow channel or through sample inlet air line 2 by the vacuum pump 12. The inlet air line 2 is heated and controlled with the temperature-controlled resistance heater 1 to within a few degrees of the sample dry-bulb temperature to prevent condensation of the moisture in the line. Dry-bulb temperature is measured with the dry-bulb RTD 3, and the air sample is then divided into two streams. One stream flows through the outer flow channel 47 and over the water supply wick 46. The other stream flows inside the inner water supply tube 38, through the inner air flow channel entrance 43, over the wet-bulb wick 35, through inner flow channel 49, and out the channel exit 44. Both streams of nearly-saturated air are mixed in the air sample exit line 6 before entering the heating coil 7 to the water preheat tank 8. Since the sample air entering the heating coil is close to the wet-bulb temperature, the water in the water preheat tank is brought close to the wet-bulb temperature. Any condensate formed in the air line is removed by the condensate drain 13 before the sample air is expelled from the device by the vacuum pump 12. Heated water, supplied at the bottom end of the psychrometer 4 flows out the small water supply ports 45 in the inner water supply tube 38. The water supply wick 46 is located just below the ports. The water has its temperature changed by evaporation of the air flowing over the water supply wick 46. This heat transfer causes the water in the tube to approach the sample air wet-bulb temperature, and thus water is supplied to the wet-bulb wick 35 near the wet-bulb temperature. Periodically, water is added to the water preheat tank 8 through the water fill line 9, whenever the level is low as indicated by the water preheat tank level indicator 63. Also, the overflow tank 17 is periodically drained.

The electrical signals from dry-bulb temperature RTD line 20 and wet-bulb temperature line 21 were corrected for measurement errors with the reference resistors before calculating temperatures in the microprocessor. Twenty values are taken and averaged to reduce sampling error in determining wet- and dry-bulb temperatures. These temperatures were then used to calculate humidity ratio and enthalpy by the equations described previously. All four values are displayed on a monitor screen 65.

EXAMPLE

The following example is given to facilitate a more detailed and better understanding of the capability of the present invention and are not intended to limit this invention to this example.

Humid air streams of controlled humidity and temperature were sampled by the energy meter of this invention and DB and WB temperatures and enthalpy obtained are found in the following table:

| DB temp. | WB temp. | Enthalpy, Btu/lb dry air | |
|---|---|---|---|
| °F. | | Energy meter | Calibration |
| 145 | 135 | 178.3 | 186.6 |
| 191 | 160 | 374.3 | 376.9 |
| 215 | 160 | 365.1 | 364.1 |
| 241 | 146 | 241.7 | 227.8 |
| 258 | 159 | 352.7 | 359.8 |
| 282 | 171 | 534.2 | 523.7 |
| 301 | 169 | 505.2 | 518.7 |
| 310 | 166 | 449.5 | 435.5 |

Calibration values were determined by adiabatically mixing a cooler and less humid air stream with the humid air stream measured by the energy meter such that the new stream was below 170° F. Thus, the humidity could be accurately measured with a standard thin film capacitor relative humidity probe and enthalpy calculated. The difference between energy meter and calibration is at most 14 Btu/lb dry air and is at most 6 percent of calibration value.

We claim:

1. A process for measuring the humidity of a gas comprising,
    drawing a sample of said gas through a first tube,
    heating said tube to within a few degrees of the dry bulb temperature of the gas sample to prevent condensation within the tube,
    measuring the dry bulb temperature of the sample,
    delivering the sample to a housing and dividing it into two streams, said housing circumscribing a cylinder partially filled with water, said cylinder including supply ports, a wick being located on the exterior of said cylinder below said ports,
    one of said streams flowing around said cylinder and wick and exiting from said housing through an outlet, the second of said streams flowing into said cylinder through an entrance and into contact with a wet-bulb wick circumscribing a wet-bulb sensing device,
    measuring the wet-bulb temperature of the sample,
    discharging the second stream from the cylinder and combining it with the first stream,
    extracting heat from said combined streams and transferring it to the water to be delivered to the cylinder,
    calculating the enthalpy of the sample.

2. The method of claim 1 including calculating the humidity ratio of the sample.

3. Apparatus for measuring temperatures and calculating the humidity ratio and enthalpy of a sample of gas including,
    two temperature sensing devices, a housing having a vertical cylinder mounted therein, a tube for delivering a sample of gas to said housing, a channel for exhausting gas from said housing, a water supply means for delivering water from a source to the interior of said cylinder and means for heating the water at said source by heat exchange with said gas from said exhaust channel,
    means for heating said tube to within a few degrees of the dry-bulb temperature of said gas sample,
    the first of said temperature sensing devices being located to measure the temperature of the gas sample between the heating means and the housing, the second of said temperature sensing devices being located within said cylinder and a wet wick circumscribing the second device, the water in the cylinder leaking from within through a plurality of ports to wet a wick below said parts and circumscribing said cylinder, an entrance into the cylinder from said housing, said entrance being located above said ports, an exit from the cylinder and the housing for gas flowing into the cylinder from the entrance, the second temperature sensing device being located in the cylinder in the flow path between the entrance and the exit.

4. The apparatus of claim 3 including a pump for drawing the sample into the housing and subsequently past the water supply means.

5. A psychrometer for measuring the humidity of a gas flow, comprising;

a first sensor for measuring the dry bulb temperature of said gas flow;

a second sensor for measuring the wet bulb temperature of said gas flow;

a wick surrounding said second sensor and capable of absorbing a volatile liquid;

liquid supply means for supplying said volatile liquid to said wick adjacent said second sensor; and liquid preheater means for heating said volatile liquid to a temperature within about 5° C. of said wet bulb temperature sensed by said second sensor before said liquid is supplied to said liquid supply means, a housing encompassing said psychrometer including a handle for manual transportation of the psychrometer, a plurality of openings in said housing to allow the reading of gauges and screens and to service the enclosed equipment.

* * * * *